US00PP29968P2

(12) United States Plant Patent
Opsteen

(10) Patent No.: US PP29,968 P2
(45) Date of Patent: Dec. 11, 2018

(54) ***GYMNOCLADUS* TREE NAMED 'MCKBRANCHED'**

(50) Latin Name: *Gymnocladus dioicus*
Varietal Denomination: McKBranched

(71) Applicant: McKay Nursery Company, Waterloo, WI (US)

(72) Inventor: Aaron M Opsteen, Waterloo, WI (US)

(73) Assignee: MCKAY NURSERY COMPANY, Waterloo, WI (US)

( * ) Notice: Subject to any disclaimer, the term of this patent is extended or adjusted under 35 U.S.C. 154(b) by 51 days.

(21) Appl. No.: 15/530,367

(22) Filed: Jan. 3, 2017

(51) Int. Cl.
*A01H 5/00* (2018.01)

(52) U.S. Cl.
USPC ..... Plt./216

(58) Field of Classification Search
USPC ..... Plt./216
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Gymnocladus* plant named, 'McK-Branched', that is characterized by its increased branching on trees of a young age, which is not commonly observed in plants of *Gymnocladus* and its male flowers resulting in a seedless plant.

2 Drawing Sheets

Botanical classification: *Gymnocladus dioicus*.
Variety denomination: 'McKBranched'.

BACKGROUND OF THE INVENTION

The present invention relates to a new and distinct cultivar of *Gymnocladus dioicus*, and will be referred to hereafter by its cultivar name, 'McKBranched'. 'McKBranched' is a deciduous tree grown for use as a landscape plant.

'McKBranched' was discovered by the Inventor in June of 2008 as a chance seedling growing in a production field in Waterloo, Wis. The field was planted with seedlings from seed derived from unnamed and unpatented plants *Gymnocladus dioicus*.

Asexual propagation of the new cultivar was first accomplished by budding by the Inventor in Waterloo, Wis. in July of 2008. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'McKBranched' as a new and unique cultivar of *Gymnocladus*.

1. 'McKBranched' exhibits increased branching on trees of a young age, which is not commonly observed in plants of *Gymnocladus*.
2. 'McKBranched' exhibits male flowers resulting in a seedless plant.

Typical plants of *Gymnocladus dioicus* differ from 'McK-Branched' in being less well branched at a young age and may have male or female flowers; which would produce seed pods. 'McKBranched' can be compared to the *Gymnocladus* cultivars 'Espresso' and 'Stately Manor' (both not patented). Both 'Espresso' and 'Stately Manor' are similar to 'McKBranched' in having blooms of only male flowers and is therefore lacking seed pods. 'Espresso' differs from 'McKBranched' in having a less well-branched plant habit. 'Stately Manor' differs from 'McKBranched' in having a narrower plant habit.

BRIEF DESCRIPTION OF THE DRAWINGS

The accompanying colored photographs illustrates the overall appearance and distinct characteristics of the new *Gymnocladus*.

The photograph in FIG. 1 was taken of a two-year-old plant of 'McKBranched' as grown outdoors in the ground in Waterloo, Wis. and provides a side view of a tree of 'McKBranched' illustrating its well-branched plant habit.

Figure 1:
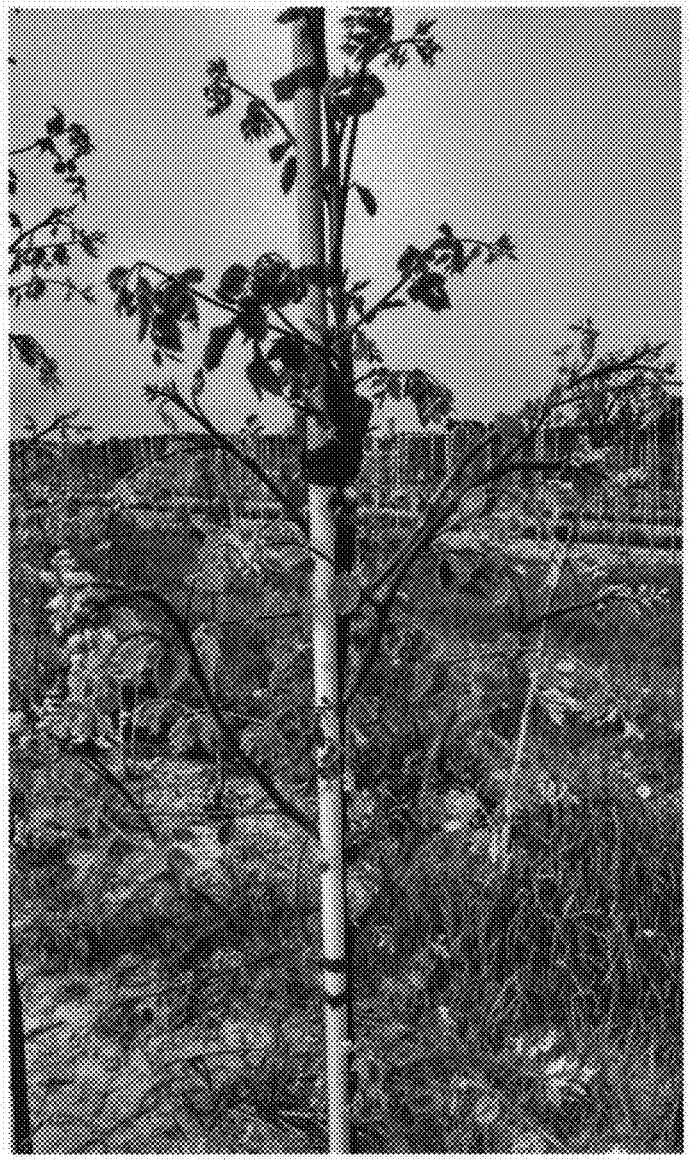
Figure 2:
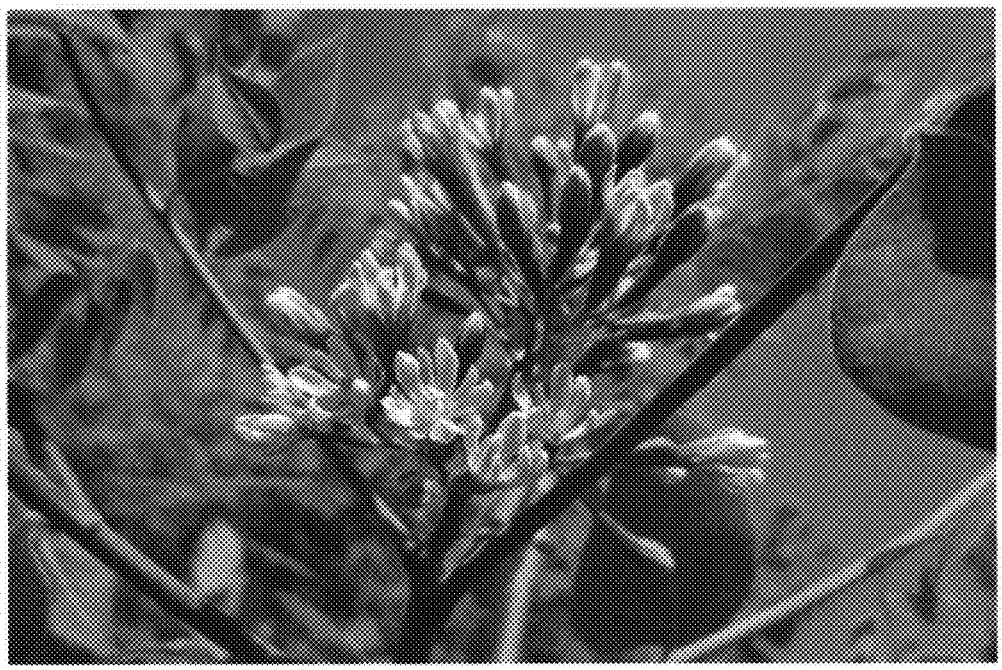

The photograph in FIG. 2 was taken of a four year-old plant of 'McKBranched' as grown in a landscape in New Hope, Minn. and provides a photo of an inflorescence.

The colors in the photograph are as close as possible with the photographic and printing technology utilized and the color values cited in the Detailed Botanical Description accurately describe the colors of the new *Gymnocladus*.

DETAILED BOTANICAL DESCRIPTION

The following is a detailed description of a three-year old plant of the new cultivar as observed growing outdoors in the ground in New Hope, Minn. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Bloom period*.—Approximately 10 days beginning in early June in Southern Wisconsin.

*Plant type*.—Deciduous tree.

*Plant habit*.—Upright, well-branched even as a young plant.

*Height and spread*.—Reaches 3 to 3.7 m in height and 1.2 to 1.8 m in spread as a three year-old plant in the ground.

*Cold hardiness*.—At least to U.S.D.A. Zone 4.

*Diseases and pests*.—Similar susceptibility and resistance to pests and diseases as compared to other cultivars of *Gymnocladus dioicus* has been observed.

*Root description*.—Deeply rooted.

*Growth rate*.—Moderate, similar to other cultivars of *Gymnocladus dioicus*.

*Propagation*.—Budding and grafting.

*Time to produce a young plant from budding*.—Budding occurs in one year, new growth is cut back in spring in year two to finish a tree 1.8 m in height, a 3.2 cm tree is obtained in 3 years.

Stem description:

*Shape*.—Rounded.

*Stem size*.—Lateral stems; an average of 1.4 cm in width and 46 to 61 cm in length, main trunk; 2.5 m in length, an average of 4 cm in width measured 1 m from base.

*Stem surface*.—Lateral stems; glabrous and with lenticels about 1 mm in length, 15 per sq. cm 197B to 197C in color, main trunk; rough barked, slightly exfoliating.

*Branching*.—Well-branched with an average of 10 lateral stems uniformly distributed along the main stem.

*Stem strength*.—Strong.

*Branch arrangement*.—Alternate to whorled.

*Branch aspect*.—Main stem is upright with lateral stems held at an average angle between 55° to 80° from the main stem (90° vertical).

*Internode length*.—An average of 4.5 cm.

*Branch color*.—Lateral branches; 198B on the sun exposed upper surface and 200B to 200C on the shaded lower surface, main trunk; 197B to 197C suffused with 199C to 199D.

Foliage description:

*Leaf arrangement*.—Leaves and secondary leaflets; alternate, leaflets; opposite to slightly alternate.

*Leaf division*.—Bipinnate.

*Leaf quantity*.—An average of 5 leaves per branch, 7 leaflets per leaf, and 10 secondary leaflets per leaflet.

*Leaf size*.—Leaf; up to 38 cm in length and 25 mm in width, leaflet; up to 14 cm in length and 6.5 cm in width, secondary leaflet; up to 4.2 cm in length and 2.2 cm in width.

*Leaf shape*.—Leaf; ovate, leaflet; oblong, secondary leaflet; ovate.

*Secondary leaflet base*.—Rounded.

*Secondary leaflet apex*.—Acute.

*Secondary leaflet venation*.—Pinnate, puberulent, color: upper and lower surfaces 144B to 144C.

*Secondary leaflet margins*.—Entire and puberulent.

*Secondary leaflet surface*.—Newly emerged leaflet upper and lower surfaces; glabrous, smooth, and shiny, mature leaflet upper and lower surfaces; smooth and dull.

*Secondary leaflet color*.—Newly emerged leaflet upper surface; 143A lightly suffused with 176B and lower surface; 143A, mature leaflet upper surface; 139A and lower surface; 137A, fall; primarily 151D on both surfaces.

*Rachis*.—Primary; rounded in shape; up to 27 cm in length and 2.5 mm in width, color; upper surface 183A and lower surface 143C, upper surface; puberulent with hairs 158B in color, secondary; rounded in shape, up to 11 cm in length and 1 mm in width, color; upper and lower surfaces 143C, upper surface lightly suffused with 183A and puberulent with hairs 158B in color, all surfaces; smooth and satiny.

*Petiole*.—An average of 1.5 mm in length and 1 mm in width, 144A in color, flexible and moderately strong, smooth, puberulent surface.

Inflorescence description:

*Inflorescence type*.—Raceme of corymbs at terminals of new growth, dioecious plant; male flowers only.

*Inflorescence size*.—Average of 10 cm in height and 4.5 cm in width.

*Flower buds*.—Narrow obovate in shape, an average of 1.6 cm in length and 4 mm in diameter, calyx portion 146C and heavily suffused with 178B and petal potion a blend of 146C and 145B in color, burst in early June.

*Flower fragrance*.—None.

*Lastingness of flowers*.—About 6 days.

*Flower aspect*.—Primarily outward, upward at apex of rachis.

*Flower quantity*.—An average of 55 flower per inflorescence, about 20 inflorescences per tree.

*Flower type*.—Tubular with spreading petals and sepal tips, single.

*Flower size*.—Average of 1.2 cm in diameter (at apex) and 1.8 cm in depth.

*Peduncles*.—Rachis; an average of 8 cm in length and 3.5 mm in diameter, very strong, held nearly upward to the lateral branch, 144A in color, glaucous surface, corymb peduncles; an average of 6 mm in length and 1.5 mm in width, slightly glaucous surface with very sparse hairs, held an average angle of 45°, 144B in color.

*Pedicels*.—Average of 1 cm in length and 1 mm in diameter, held straight and to a 20° angle to peduncle, moderately strong, 145B in color, surface dull and slightly hairy.

*Calyx*.—Tubular in shape, fused tubular portion an average of 1.1 cm in length and 3.5 mm in width with spreading sepal tips 3 mm in height and 1.2 cm in diameter.

*Sepals*.—5, fused with free tips, tube; an average of 1.1 cm in length and 3.5 mm in width, color outer surface 146C and heavily suffused with 178B, color inner surface 152C, both surfaces pubescent, outer surface ribbed, tips; an average of 6 mm in length and 0.7 mm in width, linear in shape, acute apex, fused base, entire margin, rotate in arrangement, both surfaces pubescent, color: young and mature upper 146C and lower surface; 146C and slightly suffused with 178B.

*Petals*.—5, fused to top of tube with spreading lobes, lobes; narrowly oblanceolate in shape, margin entire, apex obtuse-acute, an average of 1.1 cm in length, 3 mm in width, both surfaces pubescent, color when opening and mature upper and lower surface is a blend of 146D and 145B.

Reproductive organs:

*Gynoecium*.—None, only male flowers are present.

*Androcoecium*.—5 stamens, anthers are basifixed, oblong in shape, 1 mm in length and 162D in color, filaments are an average of 3 cm in length and NN155A in color, pollen is very low in quantity and 165D in color.

*Fruit and seed*.—No fruit or seed is produced as they are male flowers.

It is claimed:

1. A new and distinct cultivar of *Gymnocladus* plant named 'McKBranched' as herein illustrated and described.

* * * * *